US011679156B2

(12) United States Patent
Jacksier et al.

(10) Patent No.: US 11,679,156 B2
(45) Date of Patent: Jun. 20, 2023

(54) USE OF STABLE ISOTOPES TO PROVE AUTHENTICATION OF MANUFACTURING LOCATION

(71) Applicants: Tracey Jacksier, Landenberg, PA (US); Mani Matthew, Neshanic Station, NJ (US); Anthony W. Reccek, Jr., Corinth, TX (US); Martin Vasarhelyi, Middelfart (DK); Vincent M. Omarjee, Versailles (FR); L'Air Liquide, Société Anonyme pour l'Etude et l'Exploitation des Procédés Georges Claude, Paris (FR); American Air Liquide, Inc., Fremont, CA (US); Airgas, Inc., Radnor, PA (US)

(72) Inventors: Tracey Jacksier, Landenberg, PA (US); Mani Matthew, Neshanic Station, NJ (US); Anthony W. Reccek, Jr., Corinth, TX (US); Martin Vasarhelyi, Middelfart (DK); Vincent M. Omarjee, Versailles (FR)

(73) Assignees: American Air Liquide, Inc., Fremont, CA (US); Airgas, Inc., Radnor, PA (US); L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 424 days.

(21) Appl. No.: 16/873,560

(22) PCT Filed: Nov. 1, 2018

(86) PCT No.: PCT/US2018/058657
§ 371 (c)(1),
(2) Date: May 1, 2020

(87) PCT Pub. No.: WO2019/089896
PCT Pub. Date: May 9, 2019

(65) Prior Publication Data
US 2022/0296717 A1  Sep. 22, 2022

Related U.S. Application Data
(60) Provisional application No. 62/580,677, filed on Nov. 2, 2017.

(51) Int. Cl.
A61K 47/02  (2006.01)
G01N 33/00  (2006.01)
G01N 33/15  (2006.01)

(52) U.S. Cl.
CPC .......... *A61K 47/02* (2013.01); *G01N 33/0098* (2013.01); *G01N 33/15* (2013.01); *G01N 2033/0093* (2013.01)

(58) Field of Classification Search
CPC .... A61K 47/02; G01N 33/0098; G01N 33/15; G01N 2033/0093
USPC .................................................. 356/156, 330
See application file for complete search history.

(56) References Cited

U.S. PATENT DOCUMENTS

| 5,760,394 A | 6/1998 | Welle | |
|---|---|---|---|
| 2006/0035380 A1 | 2/2006 | Saint-Leger | |
| 2007/0134722 A1 | 6/2007 | Gross | |
| 2014/0230099 A1* | 8/2014 | Shirley | A45C 11/182 435/320.1 |
| 2014/0266197 A1* | 9/2014 | Kalechofsky | G01R 33/485 324/309 |

FOREIGN PATENT DOCUMENTS

| WO | WO 97 43751 | 11/1997 |
|---|---|---|
| WO | WO 2010 092202 | 8/2010 |
| WO | WO 2016 109631 | 7/2016 |

OTHER PUBLICATIONS

Soong J.L. et al., Design and operation of a continuous $^{13}$C and $^{15}$N labeling chamber for uniform or differential, metabolic and structural, plant isotope labeling, Journal of Visualized Experiments, Jan. 2014, 83, e51117, 1-8.
International Search Report and Written Opinion for corresponding PCT/US2018/058657, dated Mar. 20, 2019.

* cited by examiner

Primary Examiner — Md M Rahman
(74) Attorney, Agent, or Firm — Elwood L. Haynes; Allen E. White

(57) ABSTRACT

The disclosure relates to a manufactured composition, material or device comprising at least two different nonradioactive isotope atoms. Each nonradioactive isotope atom is present in an amount sufficient to increase the total amount of the nonradioactive isotope atom above the total amount found in the manufactured composition, material or device in the absence of adding the nonradioactive isotope atom to increase said total amount. The ratio(s) of the at least two nonradioactive isotopes in the manufactured composition, material or device are measurably different than the ratio(s) found in the manufactured composition, material or device in the absence of adding the nonradioactive isotope atom to increase said total amount.

19 Claims, No Drawings

USE OF STABLE ISOTOPES TO PROVE AUTHENTICATION OF MANUFACTURING LOCATION

CROSS REFERENCE TO RELATED APPLICATIONS

This application is a 371 of International Application No. PCT/US2018/058657, filed Nov. 1, 2018, which claims priority to U.S. Patent Application No. 62/580,677, filed Nov. 2, 2017, the entire contents of which are incorporated herein by reference.

BACKGROUND

Counterfeit pharmaceuticals, packaged foods, including baby milk powder, as well as other cash crops can cause significant safety issues as well as significant economic issues. Analytical techniques can often be used to validate country of origin or authentication of the active ingredients in pharmaceuticals. One of the most direct methods to detect counterfeit pharmaceuticals is to analyze the properties of the product itself. This can either be achieved using laboratory-based testing of purchased or seized samples. These analytical methods are especially effective when used to validate the active ingredients and chemical constitution of the dosage form itself. Owing to the complexity and time intensity of many of these methods, it is not always possible to deploy these solutions out in the markets where counterfeit drugs are most common. Some of these techniques include X-ray, atomic absorption, nuclear magnetic resonance, Fourier transform infrared spectroscopy, liquid chromatography, mass spectroscopy, and capillary electrophoresis. The complexities and time investment of these techniques can make fraud deterrence less effective.

Food fraud and adulteration is also a significant issue as some food manufacturers still manage to swindle shoppers by adding fillers or diluting the declared contents with less expensive ingredients, without the knowledge of the consumer. Natural Honey, for example, has a high nutritional value and distinctive flavor and has a significantly higher price tag than other sweeteners. As a result, intentional adulteration using low-cost invert sugar syrups such as those derived from beet, sugarcane, or corn, are used to extend product sales. Additionally, adulterated food can be a serious issue for those with food allergies. Food allergies are not the only concern; in 2008, at least six children died after some producers of the Sanlu Group in China were found to have added melamine to their products to make it look like the watered-down milk was high in protein.

Neutraceuticals: In this market space, where ingredients are sourced and then constituted into final products, there is increasing scrutiny being placed on the authenticity of base materials—geographic origin and pedigree—in addition to assay, purity specifications, etc. A method to "tag" the products with an isotopic signature would be desirable.

Plant-based Cash crops: With agriculture techniques moving towards the use of green houses, hydroponics, aquaculture, etc. the use of controlled environments to generate crops will lend itself readily to the use of isotope fingerprints to reinforce the uniqueness of the product line.

There is a growing trend to use biologicals—both as additives of benefit to food and drug formulations and as stand-alone active ingredients for therapeutic effects. Isotope signatures imparted on such products would enhance their authenticity/traceability/security features.

Cell "husbandry:" Modern "expression" techniques employ cells in artificially-controlled environments to produce active ingredients of interest. One can refer to these as "cell factories." Isotopic tags of such products would allow one to enforce traceability.

Therefore, a simple strategy to validate which production plant specific food stuff or pharmaceutical ingredients came from would be beneficial. This would help to protect human health worldwide and increase the safety of worldwide commerce, but most importantly prevent the occurrences of dumping contaminated or unsafe products on the market.

Food stuffs are not the only commodities to be adulterated or subjected to fraud. A growing threat from organized and white collar criminals pushing stolen, out of date, adulterated or fake medications is increasing making their way into pharmacies, nursing homes, hospitals and doctor's offices. At best they are suspect because they are sold outside of the regulated supply chain. At worst, they may be medically worthless or even toxic. Since 2010 nearly 1400 adverse reactions related to counterfeit drugs have been reported to the FDA.

Traceability and security of the products is therefore of high importance. For example, experts say that fake or adulterated foods cost up to 40 billion USD per year and the problem is difficult to solve owing to the large economic motivations. The industry is now focusing on ways to prevent adulteration in the first place.

SUMMARY

Solutions to accomplish the goals of ingredient authenticity, product traceability can make use of several approaches.

First, adding a stable isotopic signature into the packaging to clearly identify plant location and authenticity and secondly, growing the key ingredients in an enriched or depleted atmosphere.

Preformed plastic packaging, blister packs, are often used for small consumer goods, foods and pharmaceuticals. Blister packs are useful for protecting products against humidity, tampering and contamination for extended periods of time. Unfortunately, the usage of preformed plastic packaging has become ubiquitous, with a market of about 280 billion USD globally, thereby enabling counterfeit products to be introduced into the supply chain. Pharmaceutical blister packs typically have a headspace between the medication and the packaging. A nitrogen purge is popular for headspace management (to minimize/eliminate moisture and/or oxygen which can affect shelf life). Using modified atmospheres in food and pharmaceutical packaging is in common use today. Ideas aimed at preventing product adulteration are not new. Tagging specific molecules in products with stable isotopes to help in the identification and origin of some products (such as explosives) has been used. The introduction of a specific stable isotopic signature into medical packaging or medicine (pharmaceuticals) to validate the origin of the products is novel. The concept can also be applied to packaged foods in a similar way as modified atmosphere packaging (MAP). By validating, not only the composition of the key elements, the proposed solution would also ensure traceability to the location/plant of production to ensure proper QA procedures and make falsification of production origin increasingly complex.

Maintaining the non-reactivity of the additive gas into the packaging is important. Therefore, stable isotopes of gases such as nitrogen, krypton or xenon can be used. Nitrogen, for example, has 2 stable isotopes; $^{14}N$ and $^{15}N$. The natural abundance of $^{14}N$ in the atmosphere is 99.6337%. This means that addition of $^{15}N$ to significantly change the ratio could be analytically detected. An additional approach would be to introduce a small concentration of one of the xenon isotopes into naturally abundant nitrogen (making a mixture). Xenon has several stable isotopes (124, 126, 128, 129, 130, 131, 132 and 134), with 129 having the highest abundance. Isotopically pure xenon is quite expensive with extremely limited supplies. Differing manufacturing locations within the same company could alter the $^{129}Xe/N_2$ ratio thereby allowing differentiation and validation of the source of manufacturing.

DESCRIPTION OF PREFERRED EMBODIMENTS

In one embodiment of the present invention, a manufactured composition, material or device, or an agricultural product, comprising at least two different nonradioactive isotope atoms is provided. Each nonradioactive isotope atom is present in an amount sufficient to increase the total amount of the nonradioactive isotope atom above the total amount found in the manufactured composition, material or device in the absence of adding the nonradioactive isotope atom to increase said total amount. In other words, the manufactured composition, material or device in an unadulterated state will have a total amount of these particular nonradioactive isotopes naturally occurring. If one were to analyze a random sample of these manufactured compositions, materials or devices, there would be a statistical average total amount of these particular nonradioactive isotopes present naturally. The intent of the present invention is to introduce additional amounts of these nonradioactive isotopes in order to distinguish a particular item or lot from any other item or lot.

Additionally, the ratio(s) of the at least two nonradioactive isotopes in the manufactured composition, material or device are measurably different than the ratio(s) found in the manufactured composition, material or device in the absence of adding the nonradioactive isotope atom to increase said total amount. In other words, the manufactured composition, material or device in an unadulterated state will have a ratio of these particular nonradioactive isotopes naturally occurring. If one were to analyze a random sample of these manufactured compositions, materials or devices, there would be a statistical average ratio of these particular nonradioactive isotopes present naturally. The intent of the present invention is to introduce additional amounts of these different nonradioactive isotopes in order to produce a unique ratio and thus to distinguish a particular item or lot from any other item or lot.

There may be at least two different nonradioactive isotope atoms are present in the manufactured composition, material or device, or the agricultural product, in the place of other isotopes of the same atoms of the manufactured composition, material or device, or the agricultural product. The at least two different nonradioactive isotope atoms may be present in the manufactured composition, material or device as part of an additional component or constituent added to the manufactured composition, material or device, or the agricultural product.

The additional component may be a label, an ink printing, a blister pack comprising a gas mixture comprising the at least two different nonradioactive isotope atoms, or combinations of the foregoing. The manufactured composition, material or device, or the agricultural product, may be a manufactured pharmaceutical product, a manufactured nutraceutical product, a manufactured chemical intermediate suitable for use in producing other products, or combinations of the foregoing.

Each of the at least two nonradioactive isotope atoms may be selected from deuterium (2D or 2H, hydrogen isotope), helium-3 (3He), carbon-13 (13C), nitrogen-15 (15N), oxygen-17 (17O), oxygen-18 (18O), fluorine-19 (19F), neon-21 (2Ne), sulfur-33 (33S), sulfur-36 (36S), argon-36 (36Ar), argon-38 (38Ar), potassium-40 (40K), calcium-42 (42Ca), calcium-43 (43Ca), calcium-46 (46Ca), calcium-48 (48Ca), iron-58 (58Fe), nickel-64 (64Ni), zinc-70 (70Zn), selenium-74 (74Se), krypton-78 or 80 (78Kr, 80Kr), strontium-84 (84Sr) and Xenon-124, 126, 128, 129, 130, 131, 132 or 134 (124Xe, etc.).

Isotope "Pod" Included in Packaging

For products that are sold in a bottle or pouch, one can introduce a special "isotope" pod into the product. As an example, several medications are sold with a pouch of silica gel in the package to keep the product dry. A specially gas-filled isotope container/pod can also be included in the silica gel pouch. Additional physical markers (a barcode, manufacturing details, an RFID tag) could be added to this pod to enhance security.

Such pods (which in themselves are inert and do not affect the taste, efficacy, presentation . . . of the product) could be included in inconspicuous niches of the package. (akin to the pellet of $N_2$ in a can of Guinness Stout—except there will be no gas release!)

For botanicals, a solution is to grow key ingredients in enriched or depleted gas environments. Plants need carbon dioxide in order to grow and develop. The process by which this is done is photosynthesis. $CO_2$ concentration in ambient air has an average of about 400 ppm. If you are growing in a greenhouse or indoors, the $CO_2$ levels will be reduced as the plants use it up during photosynthesis. All plants grow well at this level but as $CO_2$ levels are raised by 1,000 ppm photosynthesis increases proportionately resulting in more sugars and carbohydrates available for plant growth. To maintain the optimal levels of $CO_2$ in greenhouses, it is typically monitored and added. By supplying $CO_2$ with adjusted carbon and or oxygen stable isotope ranges outside of the natural variations one can produce plants with a representative stable isotope composition. The other parameters affecting the isotope signatures are the water, fertilizers, soil, etc. supplied for plant growth. These can also be manipulated isotopically in concert with the gases.

For cell husbandry, similarly, the gas environments under which the cells grow can be controlled (isotopically). All food and ingredients fed to the system can also be controlled isotopically to impart unique signatures that can be used to identify and distinguish the products that are derived from the cells.

An application to the regulations pertaining to cannabis production and consumption is possible. Today, cannabis grown in a particular geographical area needs to be consumed within that area—so cannabis products are not allowed to cross state borders in the US. An isotopic signature imparted to such products would reinforce the 'state-of'origin" tag.

To further prevent counterfeit the isotopic signature of the 13C/12C, 14N/15N, 18O/16O, 34S/32S, D/H could also be set to a specific value that cannot be present in natural regular uncontrolled atmosphere.

Active Pharmaceutical Ingredients

Cannabis products (e.g., THC) used for medicinal applications would benefit from an authenticity tag. As a botanical, the strength, quality, efficacy, purity, etc. of the product is expected to be influenced by the attention paid during the growing stage of the cannabis plant. By imparting an isotope signature to such products, one would enhance the certificate of origin, security, and authenticity of the product.

Leak-Detection

Food Inline testing has various advantages over other intrusive leak-detection methods (needle, immersion testing) that are slow and costly and usually relying on statistical sampling. This further increase the operation cost if a leak is found, the whole batch being processed is presumed to be compromised and discarded. Inline and non-intrusive methods are therefore very interesting methods for the food industry. Current existing in-line processes rely on the addition of a traceable gas. However, H2 for example could raise some obvious safety concerns in case of equipment malfunction and complexify the manufacturing process requiring the addition of another gas which only function is to be leak-detection. The present invention relies on the use of the standard atmosphere of the package such as CO2 and N2 traditionally used to preserve food taste and extend shelf-life. Instead of adding another gas such as H2, the invention here proposes to dope the already used CO2 or N2 with 13C, 18O, 15N values that are significantly higher than the standard values in the atmosphere and can be measured by laser based equipment such as CRCS with very high sensitivity to variation of 13C values in CO2 of other isotopes. This technique could be further extended to other industry performing leak detection is performed.

How to Analyze Isotopes

GCMS (Gas Chromatograph/Mass Spectrometer)

Scanning MS instruments cannot detect subtle variations in stable isotopic composition of organic molecules at natural abundance level. Standard MS instruments are equipped with a single detector, an electron multiplier not an ion counter. As a consequence, repeated measurements of the same masses in the same compound are not accurate enough for isotope ratio measurement at natural abundance level. The RSD of MS measurements is 10% (5% at best), which is not good enough to accurate measure difference in natural abundance at a level of 0.001 atom % or less. Conventional scanning MS systems can only be used to detect isotopic enrichment levels in excess of 0.5 atom % above natural abundance.

IRMS (Isotope Ratio Mass Spectrometer)

Instrumentation and methods exist for highly precise analyses of the stable-isotopic composition of organic compounds separated by GC. The general approach combines a conventional GC, a chemical reaction interface, and a specialized isotope ratio mass spectrometer (IRMS). Most existing GC hardware and methods are amenable to isotope-ratio detection. The interface continuously and quantitatively converts all organic matter, including column bleed, to a common molecular form for isotopic measurement. C and N are analyzed as CO2 and N2, respectively, derived from combustion of analytes. H and O are analyzed as H2 and CO produced by pyrolysis/reduction. IRMS instruments are optimized to provide intense, highly stable ion beams, with extremely high precision realized via a system of differential measurements in which ion currents for all major isotopologs are simultaneously monitored. Calibration to an internationally recognized scale is achieved through comparison of closely spaced sample and standard peaks. Such systems are capable of measuring 13C/12C ratios with a precision approaching 0.1‰ (for values reported in the standard delta notation), four orders of magnitude better than that typically achieved by conventional "organic" mass spectrometers. Detection limits to achieve this level of precision are typically a1 nmol C (roughly 10 ng of a typical hydrocarbon) injected on-column. Achievable precision and detection limits are correspondingly higher for N, O, and H, in that order.

NMR (Nuclear Magnetic Resonance) (Site-Specific Isotope Fractionation)

Traditional NMR can be used. SNIF NMR is commercially available.

CRDS (Cavity Ring-Down Spectroscope)

Cavity ringdown can be used to measure isotopes and isotopologues.

What is claimed is:

1. A manufactured composition, material or device, or an agricultural product comprising at least two different nonradioactive isotope atoms,
   a) wherein each nonradioactive isotope atom is present in an amount sufficient to increase the total amount of the nonradioactive isotope atom above the total amount found in the manufactured composition, material or device in the absence of adding the nonradioactive isotope atom to increase said total amount, and
   b) wherein the ratio(s) of the at least two nonradioactive isotopes in the manufactured composition, material or device are measurably different than the ratio(s) found in the manufactured composition, material or device in the absence of adding the nonradioactive isotope atom to increase said total amount,
   wherein the at least two different nonradioactive isotope atoms are present in the manufactured composition, material or device as part of an additional component or constituent added to the manufactured composition, material or device, or the agricultural product, and
   wherein the additional component is a label, an ink printing, a blister pack comprising a gas mixture comprising the at least two different nonradioactive isotope atoms, or combinations of the foregoing.

2. The manufactured composition, material or device, or the agricultural product of claim 1, wherein the at least two different nonradioactive isotope atoms are present in the manufactured composition, material or device, or the agricultural product, in the place of other isotopes of the same atoms of the manufactured composition, material or device, or the agricultural product.

3. The manufactured composition, material or device, or the agricultural product of claim 1, wherein the at least two different nonradioactive isotope atoms are present in the manufactured composition, material or device as part of an additional component or constituent added to the manufactured composition, material or device, or the agricultural product.

4. The manufactured composition, material or device of claim 3, wherein the additional component is a label, an ink printing, a blister pack comprising a gas mixture comprising the at least two different nonradioactive isotope atoms, or combinations of the foregoing.

5. The manufactured composition, material or device, or the agricultural product of claim 1, wherein the manufactured composition, material or device, or the agricultural product, is a manufactured pharmaceutical product, a manufactured nutraceutical product, a manufactured chemical intermediate suitable for use in producing other products, or combinations of the foregoing.

6. The manufactured composition of claim 1, wherein each of the at least two nonradioactive isotope atoms are selected from deuterium (2D or 2H, hydrogen isotope), helium-3 (3He), carbon-13 (13C), nitrogen-15 (15N), oxygen-17 (17O), oxygen-18 (18O), fluorine-19 (19F), neon-21 (2Ne), sulfur-33 (33S), sulfur-36 (36S), argon-36 (36Ar), argon-38 (38Ar), potassium-40 (40K), calcium-42 (42Ca), calcium-43 (43Ca), calcium-46 (46Ca), calcium-48 (48Ca), iron-58 (58Fe), nickel-64 (64Ni), zinc-70 (70Zn), selenium-74 (74Se), krypton-78 or 80 (78Kr, 80Kr), strontium-84 (84Sr) and Xenon-124, 126, 128, 129, 130, 131, 132 or 134 (124Xe, etc.).

7. An authentication method comprising at least a first isotope and a second isotope, wherein the first isotope and the second isotope have a predetermined relative mass ratio, wherein the predetermined relative mass ratio is different from the naturally occurring mass ratio, the method comprising incorporating the at least first isotope and the second isotope within a material during the production of the material, wherein the at least first isotope and the second isotope are added to the material during production.

8. The method of claim 7, wherein the material is a pharmaceutical.

9. The method of claim 7, wherein the material is a neutraceutical.

10. The method of claim 7, wherein the material is a chemical intermediary.

11. The method of claim 7, wherein the at least first isotope and the second isotope are added to the material before the completion of production.

12. The method of claim 7, wherein the material is a living organism.

13. The method of claim 7, wherein the material is a plant.

14. The method of claim 7, wherein the material is a botanical.

15. The method of claim 7, wherein the living organism/plant is at least partially grown in the presence of the at least first isotope and the second isotope.

16. The method of claim 7, wherein the at least first isotope and second isotope are added to a modified carbon dioxide atmosphere, in which the plant is at least partially grown.

17. The method of claim 7, wherein the at least first isotope and second isotope are added to a modified fertilizer, with which the plant is at least partially fed.

18. The method of claim 7, wherein the at least first isotope and second isotope are added to a modified soil, in which the plant is at least partially grown.

19. The method of claim 7, wherein the material is cell expression.

* * * * *